(12) United States Patent
Dandala et al.

(10) Patent No.: US 8,212,035 B2
(45) Date of Patent: Jul. 3, 2012

(54) PROCESS FOR PREPARATION OF ROSUVASTATIN CALCIUM FIELD OF THE INVENTION

(75) Inventors: Ramesh Dandala, Hyderabad (IN); Sambhu Prasad Sarma Mallela, Hyderabad (IN); Sukumar Nandi, Hyderabad (IN); Gangadhar Bhima Shankar Nandi, Hyderabad (IN); Sunil Kumar Buridipadu, Hyderabad (IN); Sivakumaran Meenakshisunderam, Hyderabad (IN)

(73) Assignee: Aurobindo Pharma Ltd., Hyderabad (IN)

( * ) Notice: Subject to any disclaimer, the term of this patent is extended or adjusted under 35 U.S.C. 154(b) by 354 days.

(21) Appl. No.: 12/449,426

(22) PCT Filed: Feb. 4, 2008

(86) PCT No.: PCT/IB2008/000290
§ 371 (c)(1),
(2), (4) Date: Aug. 8, 2009

(87) PCT Pub. No.: WO2008/096257
PCT Pub. Date: Aug. 14, 2008

(65) Prior Publication Data
US 2009/0312547 A1   Dec. 17, 2009

(30) Foreign Application Priority Data

Feb. 8, 2007 (IN) .............................. 277/CHE/2007
May 29, 2007 (IN) ........................... 1121/CHE/2007

(51) Int. Cl.
*C07D 239/02* (2006.01)
(52) U.S. Cl. ...................................................... 544/332
(58) Field of Classification Search .................... 544/332
See application file for complete search history.

(56) References Cited

U.S. PATENT DOCUMENTS

| | | |
|---|---|---|
| 5,260,440 A | 11/1993 | Hirai |
| RE37,314 E | 8/2001 | Hirai |
| 7,208,623 B2 | 4/2007 | Sedelmeier |
| 7,396,927 B2 | 7/2008 | Niddam-Hildesheim |
| 7,511,140 B2 | 3/2009 | Horbury |
| 7,582,759 B2 | 9/2009 | Niddam-Hildesheim |
| 2007/0037979 A1 | 2/2007 | Niddam-Hildesheim |
| 2007/0099994 A1 | 5/2007 | Niddam-Hildesheim |
| 2007/0167625 A1 | 7/2007 | Balanov |
| 2007/0191318 A1 | 8/2007 | Kumar |
| 2007/0191436 A1 | 8/2007 | Niddam-Hildesheim |
| 2007/0255060 A1 | 11/2007 | Okada |
| 2008/0188504 A1 | 8/2008 | Casar et al. |
| 2008/0234302 A1 | 9/2008 | Rafeeq |
| 2008/0255170 A1 | 10/2008 | Zlicar |
| 2009/0036680 A1 | 2/2009 | Kumar |
| 2009/0111839 A1 | 4/2009 | Zlicar |
| 2009/0187026 A1 | 7/2009 | Niddam-Hildesheim |
| 2009/0209567 A1 | 8/2009 | Niddam-Hildesheim |
| 2009/0215806 A1 | 8/2009 | Niddam-Hildesheim |
| 2009/0240054 A1 | 9/2009 | Niddam-Hildesheim |

FOREIGN PATENT DOCUMENTS

| | | |
|---|---|---|
| WO | WO 00/49014 A1 | 8/2000 |
| WO | WO 03/097614 A2 | 11/2003 |
| WO | WO 2004/014872 A1 | 2/2004 |
| WO | WO 2004/052867 A1 | 6/2004 |
| WO | WO 2006/100689 A1 | 9/2006 |
| WO | WO 2006/106526 A1 | 10/2006 |
| WO | WO 2007/000121 A1 | 1/2007 |
| WO | WO 2007/007119 | 1/2007 |
| WO | WO 2007/099561 A1 | 9/2007 |
| WO | WO 2008/044243 A2 | 4/2008 |
| WO | WO 2009/019211 A1 | 2/2009 |
| WO | WO 2009/047576 A1 | 4/2009 |

*Primary Examiner* — James O Wilson
*Assistant Examiner* — Ebenezer O Sackey
(74) *Attorney, Agent, or Firm* — Jay R. Akhave

(57) ABSTRACT

The present invention relates to an improved process for preparing (E)-7-[4-(4-fluorophenyl)-6-isopropyl-2-[methyl(methylsulfonyl)amino]pyrimidin-5-yl](3R,5S)-3,5-dihydroxyhept-6-enoic acid calcium of Formula (I).

(I)

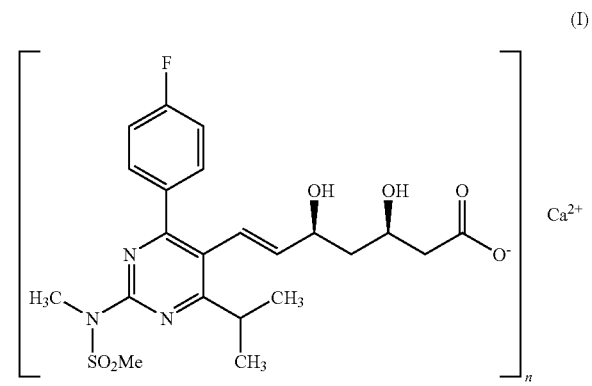

23 Claims, No Drawings

PROCESS FOR PREPARATION OF ROSUVASTATIN CALCIUM FIELD OF THE INVENTION

FIELD OF THE INVENTION

The present invention related to an improved process for preparing (E)-7-[4-(4-fluorophenyl)-6-isopropyl-2-[methyl(methylsulfonyl)amino]pyrimidin-5-yl](3R,5S)-3,5-dihydroxyhept-6-enoic acid calcium of Formula I,

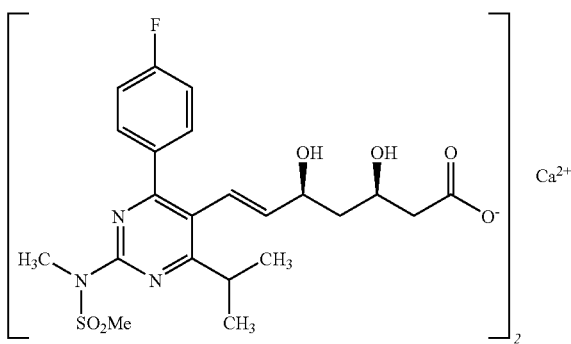

Formula I and its intermediates with high purity starting from the compound of Formula II,

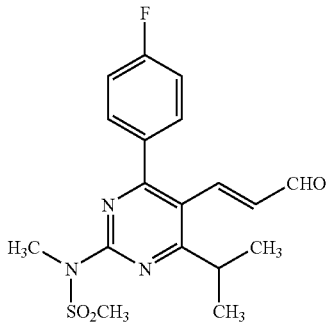

Formula II

BACKGROUND OF THE INVENTION

Rosuvastatin, which is an antihyperchlolesterolemic drug, is chemically known as (E)-7-[4-(4-fluorophenyl)-6-isopropyl-2-[methyl(methylsulfonyl)amino]pyrimidin-5-yl](3R, 5S)-3,5-dihydroxyhept-6-enoic acid calcium (2:1) salt of Formula I.

Rosuvastatin was for the first time disclosed in U.S. Pat. No. 5,260,440. Rosuvastatin is being marketed under the proprietary name CRESTOR, as an oral tablet, for the treatment of hypercholesterolemia.

In view of the importance of rosuvastatin as a lipid-lowering agent, several synthetic methods have been reported in the literature to prepare rosuvastatin, some of which are summarized below:

U.S. Pat. No. 5,260,440 disclose a process for preparing rosuvastatin in examples. The process is as shown below:

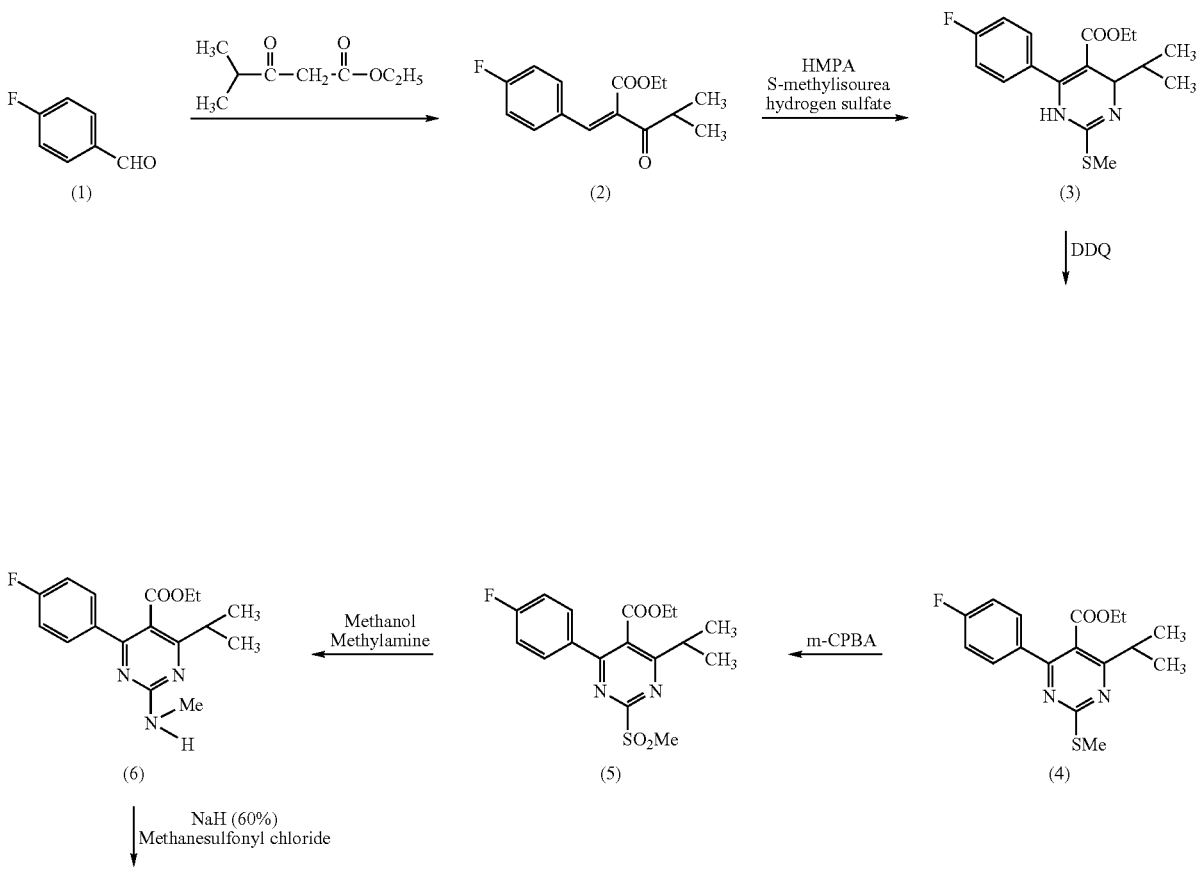

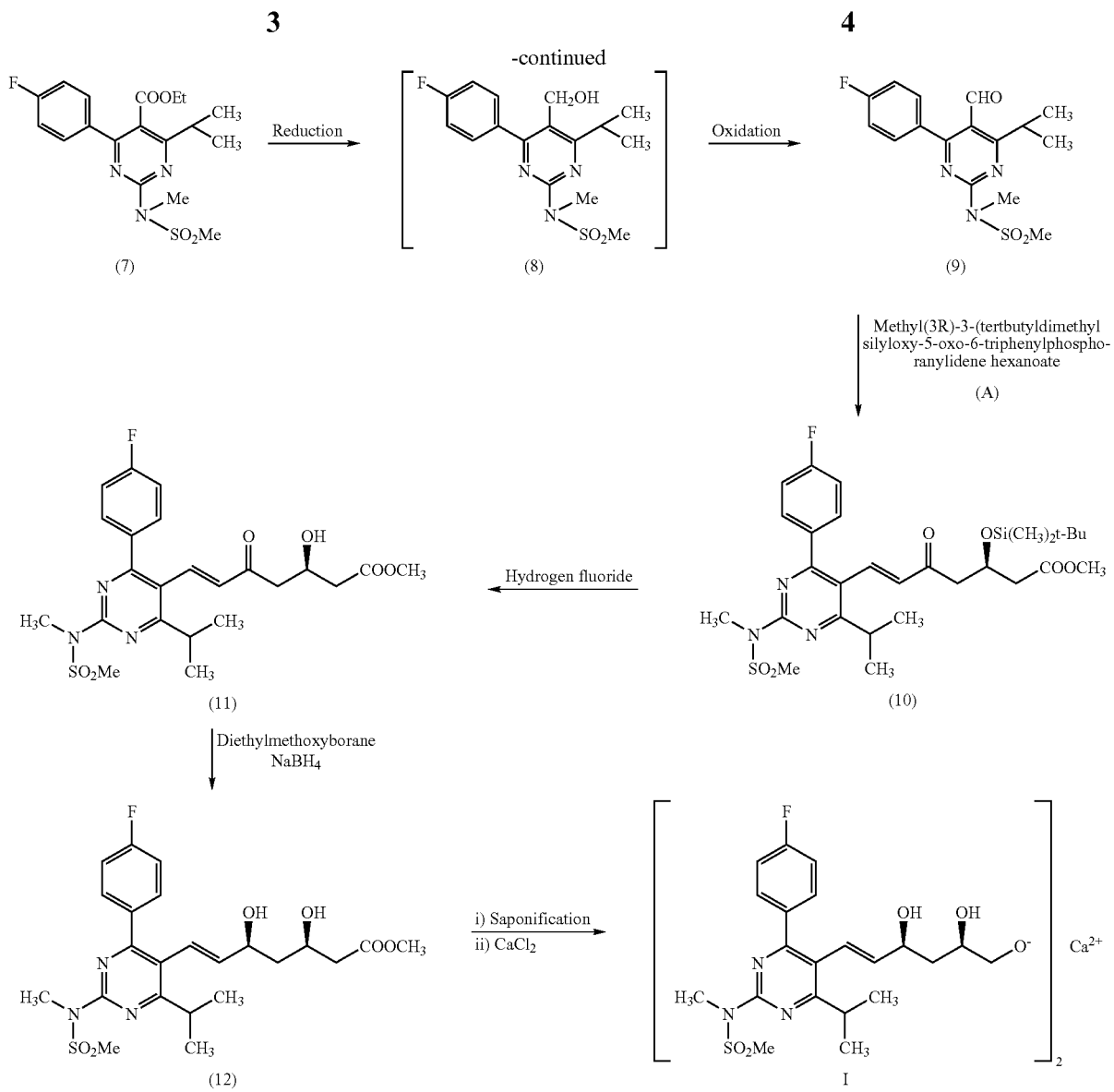

The difficulties in the above process are that the intermediate (A) is not obtained in pure form readily. Further, its purification is tedious and overall yield is extremely low. Even when intermediate (A) is obtained in pure form, further condensation with intermediate (11) to form rosuvastatin, does not result in rosuvastatin of right quality as the product contains unacceptable quantity of impurity levels.

WO 03/097614 A2 describes a modified procedure for the preparation of the starting material 4-(4-fluorophenyl)-6-isopropyl-2-[methyl(methylsulfonyl)amino]pyrimidin-5-carboxaldehyde and its further conversion to rosuvastatin by condensing with methyl (3R)-3-[(tert-butyldimethylsilyl)oxy]-5-oxo-6-triphenylphosphoranylidene hexanoate. The condensed product was deprotected using methanesulfonic acid and subsequently converted to rosuvastatin calcium (2:1) salt.

WO 2004/052867 A1 describes a process to prepare rosuvastatin by condensing 1-cyano (2S)-2-[(tert-butyldimethylsilyl)oxy]-4-oxo-5-triphenylphosphoranylidenepentane with 4-(4-fluorophenyl)-6-isopropyl-2[methyl(methylsulfonyl)amino]pyrimidin-5-carbaldehyde and subsequent deprotection of silyl group, followed by reduction and hydrolysis.

WO 2000/049014 A1 discloses a novel chemical process for the manufacture of tert-butyl (E)-(6-{2-[4-(4-fluorophenyl)-6-isopropyl-2-methyl(methylsulfonyl)amino]pyrimidin-5-yl]vinyl}-(4R,6S)-2,2-dimethyl[1,3]dioxan-4-yl)acetate, which comprises reaction of diphenyl {4-(4-fluorophenyl)-6-isopropyl-2[methyl(methylsulfonyl)amino]pyrimidin-5-yl-methyl}phosphineoxide with tert-butyl 2-[(4R,6S)-6-formyl-2,2-dimethyl-1,3-dioxan-4-yl]acetate and its further conversion to rosuvastatin.

WO 2004/014872 A1 describes a process for the manufacture of rosuvastatin calcium (2:1) salt, which comprises mixing a solution of calcium chloride with a solution of water soluble salt of (E)-7-[4-(4-fluorophenyl)-6-isopropyl-2-[methyl(methylsulfonyl)amino]pyrimidin-5-yl](3R,5S)-3,5-dihydroxyhept-6-enoic acid. This process for the preparation of rosuvastatin employs the use of phosphorane side chain, the preparation of side chain requires eight synthetic steps and involves expensive reagents. The process is both uneconomical and time consuming, hence not appropriate for commercial scale operation.

WO 2006/100689 A1 discloses a process for preparation of rosuvastatin as shown below:

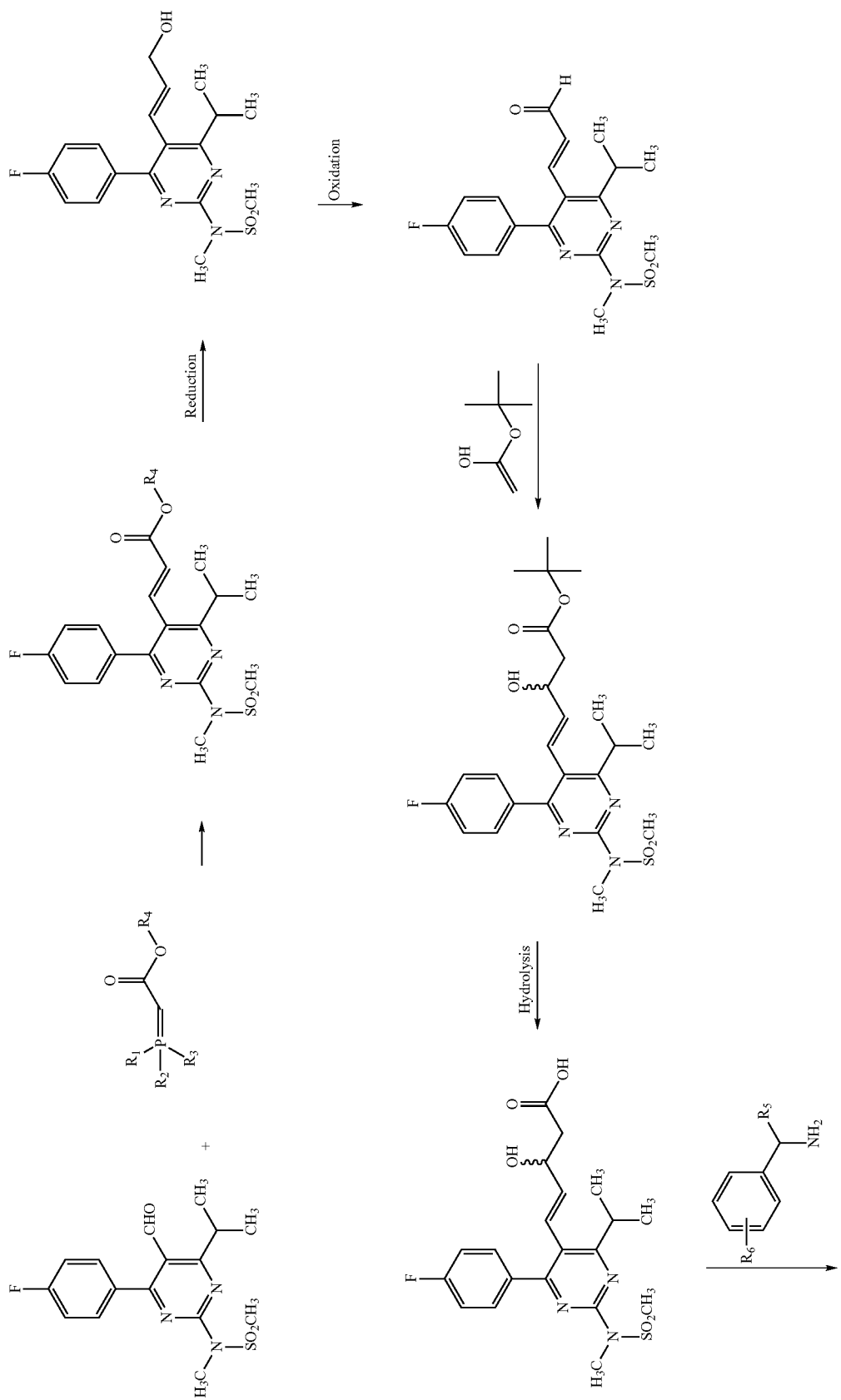

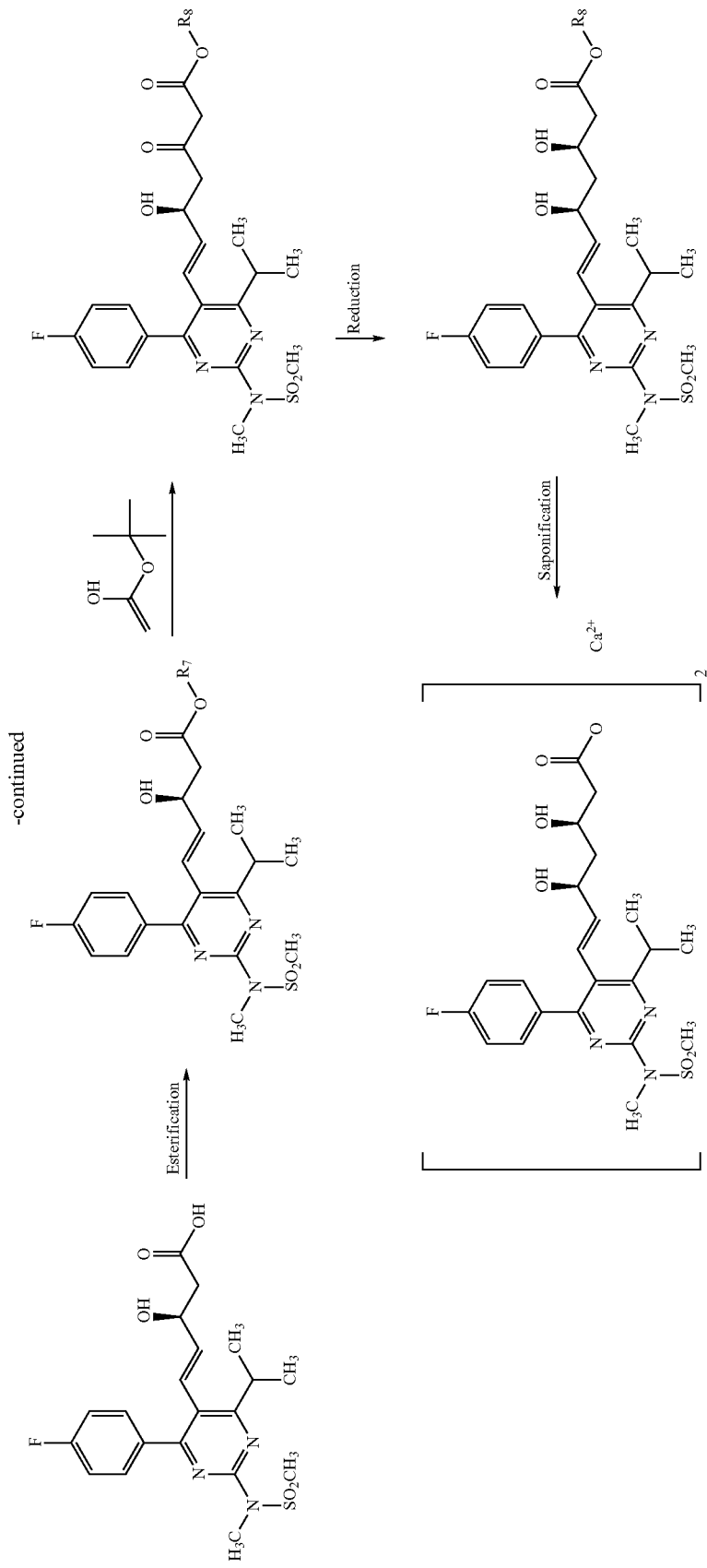

In the above scheme $R_1$, $R_2$, $R_3$ represent substituted or unsubstituted phenyl and $R_4$ represents an aliphatic residue selected from $C_1$-$C_4$ alkyl, $R_5$ represents $C_1$-$C_4$ alkyl which is optionally substituted by hydroxyl, $R_6$ represents hydrogen, halogen, $C_1$-$C_4$ alkyl or $C_1$-$C_4$ alkoxy, $R_7$ represents aliphatic residue, $R_8$ represents $C_1$-$C_4$ alkyl.

WO 2006/106526 A1 describes the preparation of rosuvastatin as shown below:

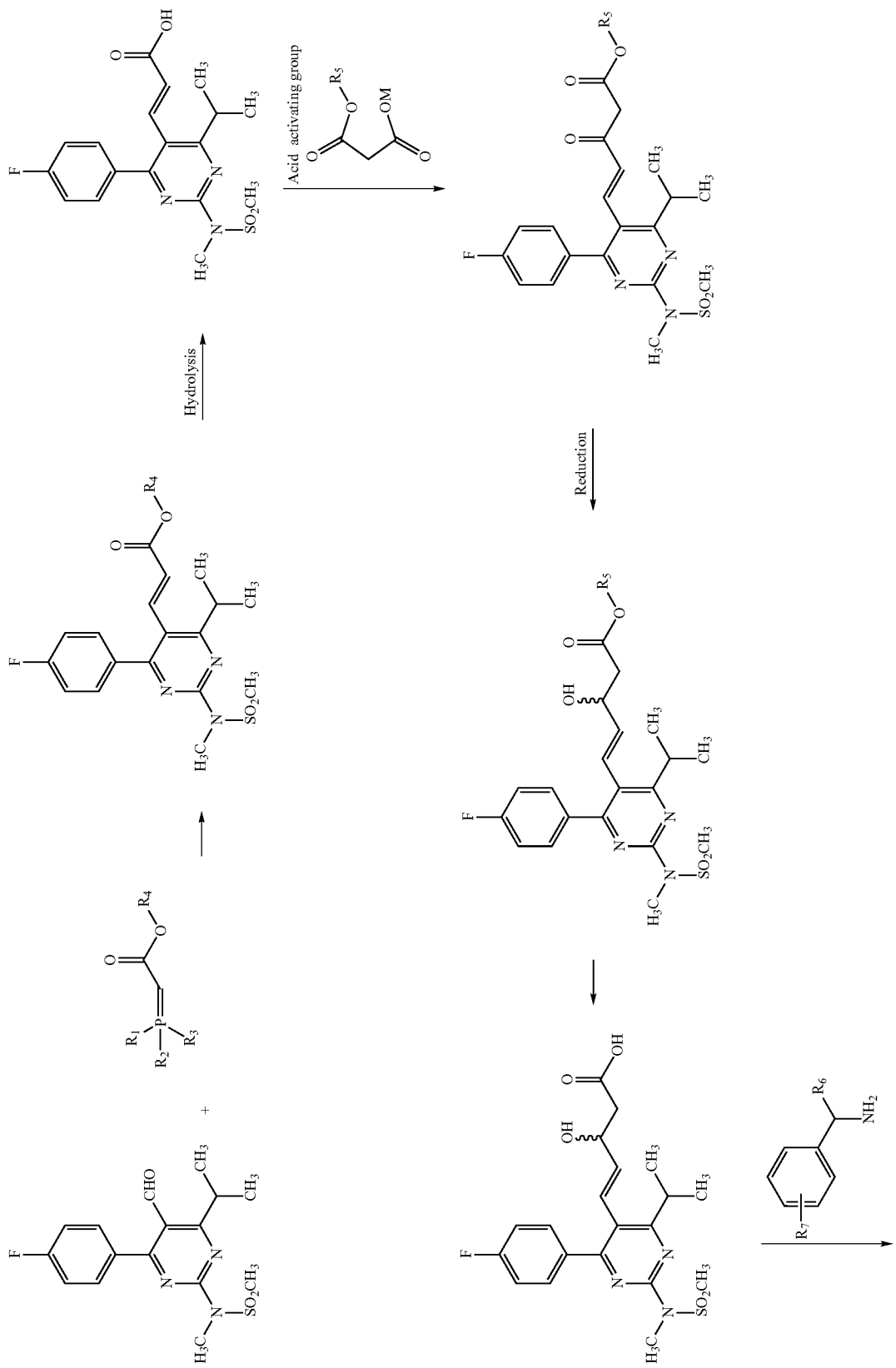

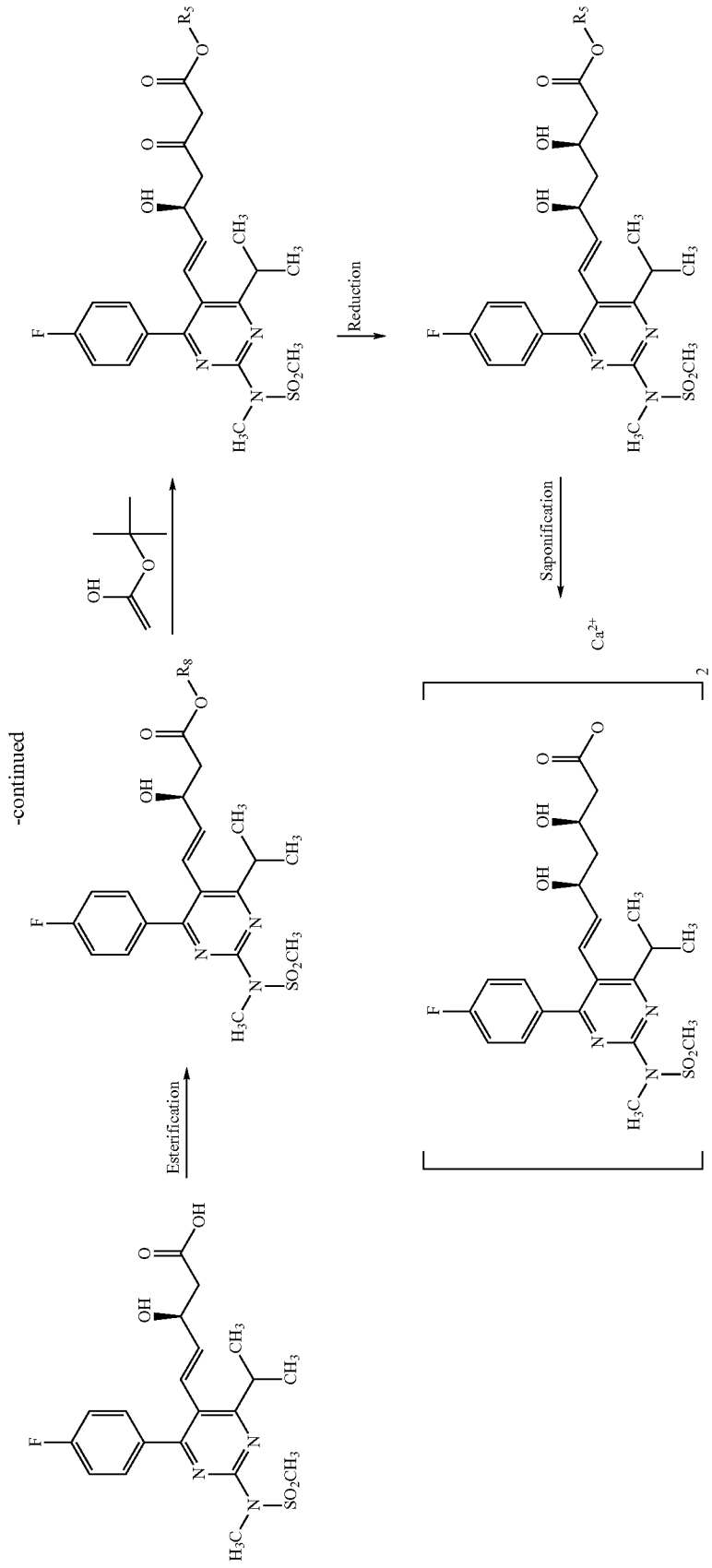

In the above mentioned scheme $R_1$, $R_2$, $R_3$ are substituted or unsubstituted phenyl and $R_4$ is an aliphatic residue selected from $C_1$-$C_4$ alkyl, $R_5$ represents $C_1$-$C_4$ alkyl, M is an alkali metal salt, X represents a halogen, $R_6$ represents $C_1$-$C_4$ alkyl which is optionally substituted by hydroxyl, $R_7$ represents hydrogen, halogen, $C_1$-$C_4$ alkyl or $C_1$-$C_4$ alkoxy, $R_8$ is an aliphatic residue selected from $C_1$-$C_4$ alkyl.

As mentioned above though there are a number of processes available, still there is a continuing need to identify alternative processes for the manufacture of rosuvastatin and its pharmaceutically acceptable salts. Such processes may, for example, when compared to previously known processes, be more convenient to use, be more suitable for large scale manufacture, give the product in a better yield, reduce the number of steps involved, use intermediates which are more easily isolated, require less complex purification techniques, use less expensive reagents and/or be more environmentally friendly.

We have now found an improved process for preparing (E)-7-[4-(4-fluorophenyl)-6-isopropyl-2-[methyl(methylsulfonyl)amino]pyrimidin-5-yl](3R,5S)-3,5-dihydroxyhept-6-enoic acid calcium of Formula I

OBJECTIVE

The objective of the present invention is to provide an improved process for preparing (E)-7-[4-(4-fluorophenyl)-6-isopropyl-2-[methyl(methylsulfonyl)amino]pyrimidin-5-yl](3R,5S)-3,5-dihydroxyhept-6-enoic acid calcium with high yield and high purity.

In yet another objective of the present invention is to provide an improved process for preparing (E)-7-[4-(4-fluorophenyl)-6-isopropyl-2-[methyl(methylsulfonyl)amino]pyrimidin-5-yl](3R,5S)-3,5-dihydroxyhept-6-enoic acid calcium, which is simple, industrially applicable and economically viable.

SUMMARY OF THE INVENTION

The present invention relates to an improved process for preparing (E)-7-[4-(4-fluorophenyl)-6-isopropyl-2-[methyl(methylsulfonyl)amino]pyrimidin-5-yl](3R,5S)-3,5-dihydroxyhept-6-enoic acid calcium of Formula I,

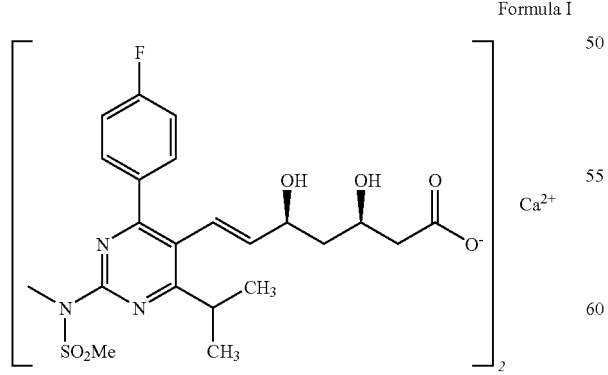

Formula I which comprises,
a) protecting the compound of Formula III with a suitable hydroxy protecting group

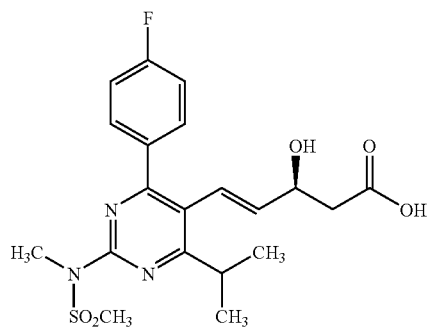

Formula III in an organic solvent to obtain a compound of Formula IV,

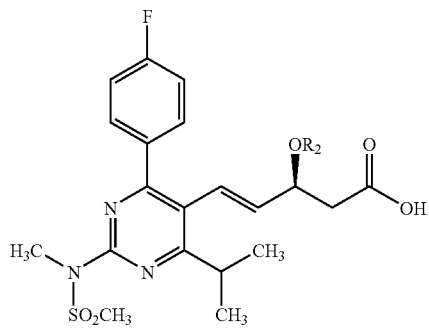

Formula IV wherein $R_2$ represents a hydroxy protecting group
b) activating the acid group of the compound of Formula IV with acid activator, followed by treating the resulting intermediate with a metal complex of Formula V,

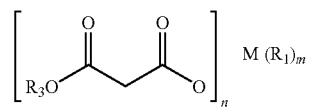

Formula V wherein $R_3$ represents $C_{1-4}$ straight chain or branched chain alkyl, aryl, substituted aryl, aralkyl; M represents Mg, Zn, Ca, Cu; n represents an integer selected from 1-3; $R_1$ represents alkyl or alkoxy; m represents an integer selected from 0 or 1; in an organic solvent to obtain a compound of Formula VI,

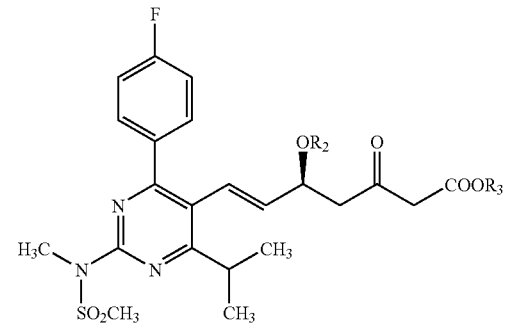

Formula VI wherein $R_3$ is as defined above, c) deprotecting the compound of Formula VI with a suitable reagent in an organic solvent, water or mixtures thereof to obtain compound of Formula VII, Formula VII

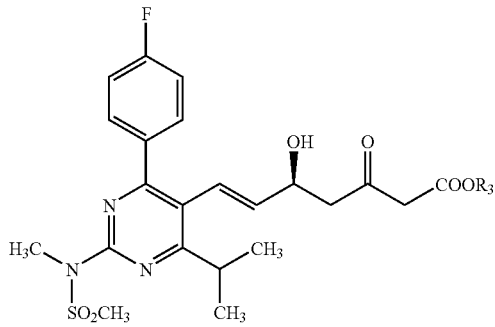

wherein $R_3$ is as defined above, d) reducing the compound of Formula VII to obtain a compound of Formula VIII, Formula VIII

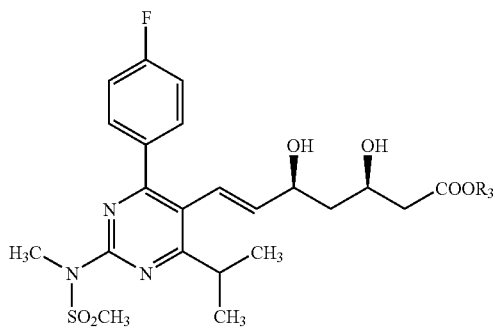

wherein $R_3$ is as defined above, e) hydrolyzing the compound of Formula VIII and converting into a salt of Formula I thereof.

DETAILED DESCRIPTION OF THE INVENTION

The compound of Formula III is protected with a suitable hydroxy protecting group selected from tert-butyldimethylsilyl chloride, dihydropyran, trimethylsilylchloride, methoxymethyl chloride, more preferably tert-butyldimethylsilyl chloride. The hydroxy protection is carried out in an organic solvent in presence of bases like imidazole, triethylamine. The usage of base is essential for completion of silylation. The organic solvent used for the above silylation reaction is selected from tetrahydrofuran, dimethoxy ethane, dioxane, dichloromethane, ethylene dichloride, N,N-dimethylformamide, dimethylsulfoxide, N-methylpyrrolidinone, sulfolane, more preferably N,N-dimethylformamide etc. Also during this silylation reaction a suitable additive is added to accelerate silylation, which is selected from sodium iodide, potassium iodide, lithium iodide etc. The reaction is conducted at a temperature in the range of 0-128° C., more preferably 50-80° C. The compound of Formula IV is isolated as an oily mass, which is sufficiently pure for the next step.

The hydroxy protected compound of Formula IV is treated with acid activator like 1,1-carbonyldiimidazole, or methyl chloroformate, ethyl chloroformate, phenyl chloroformate, 4-methoxyphenylchloroformate, 4-chlorophenylchloroformate, 2,4-dinitrophenylchloroformate, 4-trifluoromethylphenylchloroformate, 4-nitrophenylchloroformate, 2-nitrophenylchloroformate, etc, more preferably 1,1-carbonyldiimidazole. This reaction is carried out in presence or absence of organic base. The organic base is selected from triethylamine, pyridine etc. The resulting activated imidazolimide intermediate is subsequently treated with magnesium complex of monoalkyl malonate or zinc complex of monoalkyl malonate.

Magnesium complex of monoalkyl malonate can be prepared by treating 2 moles of malonic acid mono alkyl ester with 1 mole of magnesium ethoxide. This homologation is conducted at a temperature between 0-100° C., preferably at ambient temperature. The organic solvent used in the homologation is selected from tetrahydrofuran, N,N-dimethylformamide, methylene dichloride, acetonitrile or mixtures thereof.

Zinc complex of monoalkyl malonate can be prepared using different methods.

Process 1:

Zinc complex is prepared by reacting dialkyl zinc with 2 moles of lower alcohol, preferably ethanol in an inert solvent such as tetrahydrofuran, toluene, hexane, methyl tert-butyl ether, isopropyl ether or mixtures thereof, at −10° C. to 40° C., preferably 5 to 25° C. 1 to 5 moles of monoalkyl malonate, preferably 2 to 3 moles are added to this reaction mixture and stirred for 5 h 15 h, preferably 6-12 h.

Process 2:

Zinc complex is prepared by reacting dialkyl zinc with 1 to 5 moles of monoalkyl malonate, preferably 2 to 3 moles in an inert solvent such as tetrahydrofuran, toluene, hexane, methyl tert-butyl ether, isopropyl ether or mixtures thereof, at ambient temperature for 5 h to 15 h, preferably 6 h to 12 h.

Process 3:

Zinc complex is prepared by reacting zinc oxide with 1 to 5 moles of monoalkyl malonate in an inert solvent such as tetrahydrofuran, toluene, hexane, methyl tert-butyl ether, isopropyl ether or mixtures thereof, at ambient temperature for 5 h to 10 h. The water formed during the course of reaction is co-distilled with an inert solvent such as toluene.

The metal complex of Formula V, is treated with acid activated compound of Formula IV, in an inert solvent such as tetrahydrofuran, acetonitrile, toluene, methyl tert-butyl ether, isopropyl ether or mixtures thereof, at 0° to 40° C., preferably 10° C. to 25° C. for 8 h to 25 h, preferably 10 h to 24 h to yield a compound of Formula VI. During the workup of this reaction, a compound of Formula VI a, which is generated in situ Formula VI a

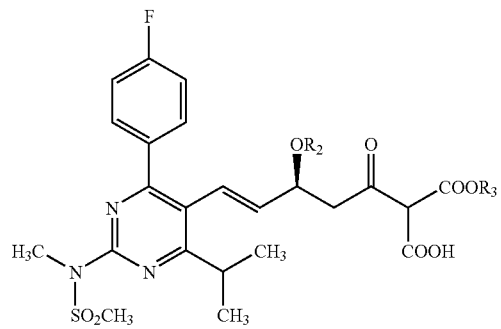

gets decarboxylated giving directly ketoester of Formula VI.

The deprotection of the compound of Formula VI to yield product of Formula VII, is carried out using acids having a general Formula HX wherein X represents halide or MX wherein X represents halogen, M is cation derived from inorganic metal like $Na^+$, $K^+$, $Li^+$ etc or organic amine like $N^+(R)_4$ where in R represents $C_1$-$C_4$ alkyl, straight or branched chain alkyl sulfonic acids such as para toluene sulfonic acids, methanesulfonic acids, trifluormethane sulfonic acid, organic acids such as formic acid, trifluroacetic acid, acetic acid in aqueous solvent or in a mixture of organic solvent at room temperature. The reaction is preferably conducted in organic solvent, water or mixtures thereof. The organic solvent can be selected from tetrahydrofuran, acetonitrile, methanol, ethanol, dichloromethane, ethylene dichloride, toluene, xylene etc.

The compound of Formula VII is stereoselectively reduced with metal borohydride in presence of chelating agent like trialkylborane or boronates selected from dialkyl alkoxy boran such as diethyl methoxy borane, diethyl ethoxy borane, dimethyl ethoxy borane, dimethyl methoxy borane, more preferably diethyl methoxy borane. The stereoselective reduction is carried out in a mixture of inert solvent preferably tetrahydrofuran and lower alkanol, more preferably methanol at −78° C. to −0° C. The metal borohydride employed is selected from sodium borohydride, potassium borohydride, calcium borohydride, more preferably sodium borohydride. After completion of reaction, excess borohydride is destroyed by acetic acid and resulting compound of Formula VIII is extracted into an organic solvent. The organic layer is concentrated under reduced pressure to give crude compound of Formula VIII, which is purified or used as such for hydrolysis.

Saponification of compound of Formula VIII is carried out using a base, such as alkali metal hydroxide selected from sodium hydroxide, potassium hydroxide, calcium hydroxide. Preferably sodium hydroxide is used. The sodium salt of rosuvastatin thus obtained can be optionally isolated or the solution containing of rosuvastatin sodium is treated with benzathine acetate to get the corresponding benzathine salt, which can be further converted to rosuvastatin calcium. Alternatively, aqueous sodium salt of rosuvastatin can be treated with calcium ion source to give rosuvastatin calcium.

The compound of Formula III,

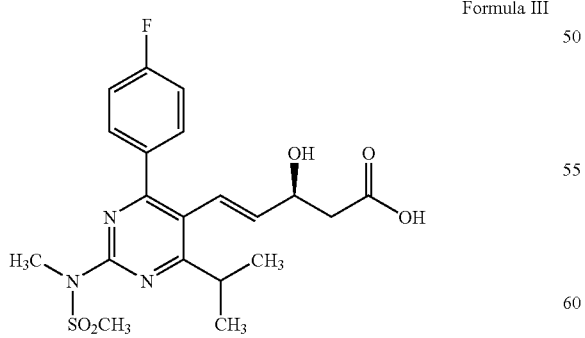

Formula III is prepared by a process which comprises.
 a) reacting (2E)-3-[4-(4-fluorophenyl)-6-isopropyl-2-(N-methyl-N-methanesulfonylamino)pyrimidin-5-yl]-propenal of Formula II,

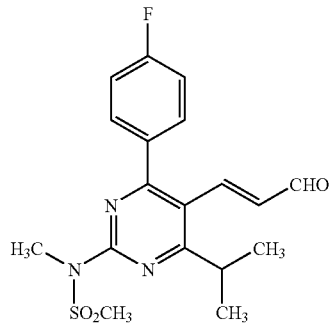

Formula II with a compound of Formula IX a or IX b

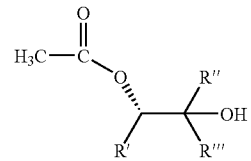

Formula IX a

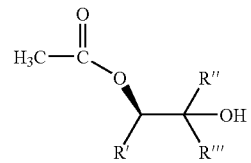

Formula IX b wherein R', R" and R''' represent alkyl, aralkyl, cycloalkyl, substituted cycloalkyl, phenyl, substituted phenyl, napthyl, substituted napthyl and heterocyclic residue, in the presence of a base and an organic solvent like ether, tetrahydrofuran, hydrocarbon solvents like heptane, hexane or mixture thereof. The preferred solvents are tetrahydrofuran and hexane. The base used in the above condensation is selected from n-butyllithium, lithium hexamethyldisilazane, sodium hexamethyldisilazane, lithium diisopropylamine, etc more preferably lithium hexamethyldisilazane. The condensation reaction is carried out at a temperature ranging from −78° C. to +20° C. After completion, the reaction is quenched with 5 N HCl and extracted with an organic solvent to give a diasteromeric mixture of compounds of Formula X a or Formula X b

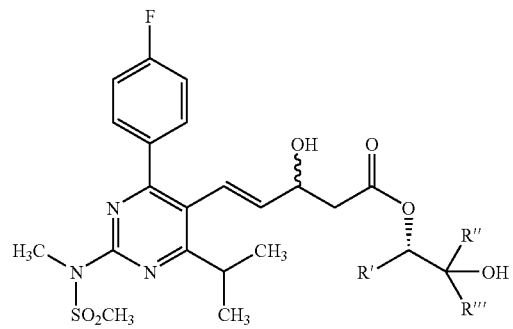

Formula X a

Formula X b

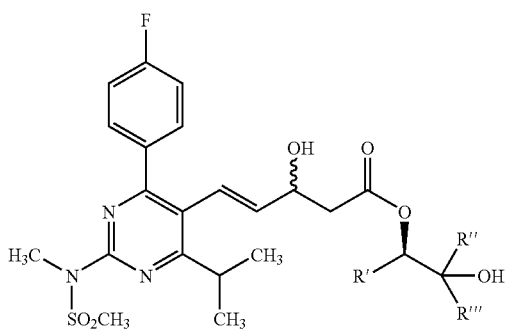

wherein R', R" and R'" are defined as above, is hydrolyzed to give the compound of Formula XI, Formula XI

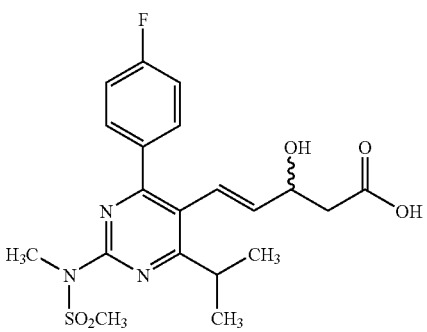

which is then resolved using optically pure precipitating agents, for example (+) or (−) phenylalkylamine or substituted phenylalkylamine, Ephedrine (+) (−), 1-amino-1-butanol (+) (−), Quinine (−), Quinidine (+), Cinchonidine (+), Brucine (−), Dehydroabietylamine (+), preferably (R)-1-phenylethylamine in a suitable organic solvent to get enantiomerically pure compound of Formula III. The organic solvent is selected from acetonitrile, tetrahydrofuran, ethyl acetate, methanol, ethanol, isopropyl alcohol or a mixture of organic solvent and water.

Formula III

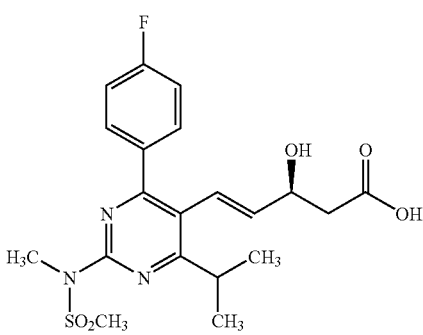

The invention is illustrated with the following examples, which are provided by way of illustration only and should not be construed to limit the scope of the invention.

Example 1

PREPARATION OF ETHYL-6-(E)-7-[4-(4-FLUOROPHENYL)-6-ISOPROPYL-2-[N-METHYL-N-METHYLSULFONYLAMINO]PYRIMIDIN-5-YL]-(5S)-5-(t-BUTYLDIMETHYLSILYLOXY)-3-OXO HEPTENOATE

20% w/v Diethyl zinc in toluene (10 ml) was added to toluene (50 ml) and cooled to 10-15° C. Ethanol (1.9 ml) was added at the same temperature to the reaction mixture and stirred for 12 h at 25-30° C. Thereafter, the resulting clear solution was treated with a solution of monoethyl malonate (3.91 g) in toluene (50 ml) and stirred for 6 h at room temperature. Ethanol, a by-product from the reaction mass was removed by co-distillation with toluene at 40-45° C. The resulting mass was diluted with toluene and further treated with a solution of Imidizolyl-(4E)-5[4-(4-fluorophenyl)-6-isopropyl-2-[N-methyl-N-methylsulfonylamino]pyrimidin-5-yl]-(3S)-3-(t-butyldimethylsilyloxy)pentenoate (6 g) in toluene (30 ml) at room temperature and the reaction mass was stirred for 40 h for completion of coupling reaction. After the reaction, mass was quenched with 5% aqueous citric acid. The separated organic layer was washed with aqueous bicarbonate and finally with water. The crude product obtained after evaporation of solvent was purified by column chromatography. (Silica gel; Hexane:Ethylacetate mixture)

Yield: 2 g $^1$HNMR (CDCl$_3$, 300 MHz): 003 (s, 6H), 0.85 (s, 9H), 1.24 (d, 6H), 1.26-1.29 (t, 3H), 2.49 (d, 1H), 2.50 (d, 1H), 2.65 (septet, 1H), 3.4 (s, 2H), 3.5 (s, 3H), 3.5 (s, 3H), 3.56 (s, 3H), 4.1 (q, 2H), 4.56-4.58 (m, 1H), 5.48 (dd, 1H), 6.55 (d, 1H), 7.1 (m, 2H), 7.58 (dd, 2H).

Example 2

PREPARATION OF ETHYL-6-(E)-7-[4-(4-FLUOROPHENYL)-6-ISOPROPYL-2-[N-METHYL-N-METHYLSULFONYLAMINO]PYRIMIDIN-5-YL]-(5S)-5-(t-BUTYLDIMETHYLSILYLOXY)-3-OXO HEPTENOATE

Zinc oxide (0.243 g) was suspended in toluene (50 ml) and monoethyl malonate (1.45 g) in toluene (10 ml) was added at 25-30° C. and stirred for 3 h. To the resulting clear solution imidazolyl-(4E)-5-[4-(4-fluorophenyl)-6-isopropyl-2-[N-methyl-N-methylsulfonylamino]-pyrimidin-5-yl]-(3S)-3-(t-butyldimethylsilyloxy) pentenoate (1.85 g) in tetrahydrofuran (5 ml) was added at 20-30° C. and stirred the reaction mass at room temperature for 18 h. After the completion of coupling reaction, the reaction mass was quenched by the addition of aqueous citric acid and the organic layer was separated and washed with aqueous sodium bicarbonate followed by water. The organic layer was concentrated to yield crude compound. The crude compound obtained after evaporation of solvent was purified by column chromatography to yield the compound in pure form.

Yield: 1.3 g

Example 3

PREPARATION OF ETHYL-6-(E)-7-[4-(4-FLUOROPHENYL)-6-ISOPROPYL-2-[N-METHYL-N-METHYLSULFONYLAMINO]PYRIMIDIN-5-YL]-(5S)-5-(t-BUTYLDIMETHYLSILYLOXY)-3-OXO HEPTENOATE

20% w/w Diethyl Zinc in toluene (10 ml) was diluted with toluene under N$_2$ atmosphere at 0-5° C. and then treated with a solution of monoethyl malonate (3.91 g) in toluene (10 ml) at 20-30° C. The resulting solution was stirred for 4 h at 25-30° C. for complex formation and further treated with imidazolyl-(4E)-5[4-(4-fluorophenyl)-6-isopropyl-2-[N-methyl-N-ethylsulfonylamino]-pyrimidin-5yl]-3-(S)-3-(t-butyldimethylsilyloxy)-pentenoate (5.5 g) in toluene (15 ml) and stirred at room temperature for 21 h for completion of coupling reaction, and product precipitates out. The crude compound obtained was purified by column chromatography.
Yield: 2.3 g

Example 4

PREPARATION OF t-BUTYL-(6E)-7-{4-(4-FLUOROPHENYL)-6-ISOPROPYL-2-[N-METHYL-N-METHYLSULFONYLAMINO]PYRIDIN-5-YL}-(5S)-5-(t-BUTYLDIMETHYLSILYLOXY)-3-OXO HEPTENOATE

Diethyl zinc (10 ml, 1M, solution in hexane) was added to tetrahydrofuran (20 ml) at 10-15° C. and a mixture of ethanol (0.92 gm, 0.02 mol) and tetrahydrofuran (2ml) was added drop wise into the above diethyl zinc solution over a period of 10-15 min. The reaction mass was stirred at the same temperature for 30 min and mono-t-butyl malonate (3.2 gm, 0.02 mol) was added to the reaction mass drop wise after diluting with tetrahydrofuran (10 ml). The mixture was stirred for two hours and imidazolyl-5-{4-(4-fluorophenyl)-6-isopropyl-2-[N-methyl-N-methylsulfonylamino]pyrimidin-5-yl}-(3S)-3-(t-butyldimethylsilyloxy]heptenoate (2.5 gm) dissolved in tetrahydrofuran (10 ml) was added to it slowly over a period of 20 min. The reaction was stirred for 16 h at 20-25° C. and quenched by adding water (20 ml) drop wise into the reaction mixture. The organic layer was separated and the aqueous layer was extracted with ethyl acetate (25 ml). The combined organic layer was washed with water (50 ml) and dried over sodium sulfate. The solvent was distilled out under reduced pressure (50-100 mm Hg) at 35-40° C. to obtain the crude product as an oily mass, which was further purified by column chromatography using hexane, ethyl acetate. (9:1 v/v) as an eluant.
Yield: 2.5 g
$^1$HNMR (CDCl$_3$, 300 MHz): 0.1 (s, 6H), 0.93 (s, QH), 1.27 (d, 6H), 1.48 (s, 9H), 2.53 (dd, 2H), 3.33 (septet, 1H), 2.36 (s, 2H), 3.53 (s, 3H), 3.58 (s, 3H), 4.53-7.55 (m, 1H), 5.52 (dd, 1), 6.58 (d, 1H), 7.01 (t, 2H), 7.62 (dd, 2H).

Example 5

PREPARATION OF t-BUTYL-(6E)-7-{4-(4-FLUOROPHENYL)-6-ISOPROPYL-2-[N-METHYL-N-METHYLSULFONYLAMINO]PYRIMIDIN-5-YL}-(5S)-5-HYDROXY-3-OXO HEPTENOATE t-Butyl(6E)-7-{4-(4-fluorophenyl)-6-isopropyl-2-[N-methyl-N-methylsulfonylamino]pyrimidin-5-yl}-(5S)-5-[t-butyl dimethylsilyloxy)-3-oxo heptenoate (2.5 gm) was dissolved in tetrahydrofuran (10 ml) at 25-30° C. and tetrabutyl ammonium fluoride (5 ml, 1M solution in tetrahydrofuran) was added to it drop wise over a period of 15 min. The mixture was stirred for 30 min at 25-30° C. and quenched with aqueous sodium carbonate (25 ml, 10% w/v). The organic layer was separated and the aqueous layer was extracted with ethyl acetate (25 ml). The combined organic layer was washed with D.M water (25 ml) and solvent was evaporated under reduced pressure at 35-40° C. to obtain the product as an oily mass. The product obtained was used as such for the subsequent reaction without further purification.
Yield: 2 g
$^1$H NMR (CDCl$_3$, 300 MHz): 1.27 (d, 6H), 1.47 (S, 9H), 2.39 (d, 2H), 3.37 (septet, 1H), 3.38 (brs, 1H), 3.53 (s, 3H), 3.58 (s, 3H), 4.51-4.53 (m, 1H), 5.5 (dd, 1H), 6.65 (d, 1H), 7.09 (f, 2H), 7.65 (dd, 2H).

Example 6

PREPARATION OF t-BUTYL-(6E)-7-{4-(4-FLUOROPHENYL)-6-ISOPROPYL-2-[N-METHYL-N-METHYLSULFONYLAMINO]PYRIMIDIN-5-YL}-(3R,5S)-3,5-DIHYDROXY HEPTENOATE t-Butyl-(6E)-7-{4-(4-fluorophenyl)-6-isopropyl-2-[N-methyl-N-methylsulfonyl-amino]pyrimidin-5-yl}-(5S)-5-hydroxy-3-oxo heptenoate (2 g, 0.003 mol) was dissolved in tetrahydrofuran (54 ml) and methanol (14 ml) at 25-30° C. under nitrogen atmosphere. The mixture was cooled to −78° C. and diethylmethoxy borane (1 ml, 48% solution in tetrahydrofuran, 0.004 mol) was added to it drop wise at −78° C. over a period of 10 min. The mixture was stirred at −75° C. to −78° C. for one hour and sodium borohydride (0.14 gm, 0.003 mol) was added to it slowly over a period of 15 min. It was stirred for 2 h at −75° C. to −78° C. and quenched by adding acetic acid (2 ml) at −78° C. Saturated aqueous sodium bicarbonate solution (50 ml) was added to it and stirred for 15 min. The organic layer was separated and aqueous layer was extracted with ethyl acetate (25 ml). The combined organic layer was washed with water (25 ml) and dried over sodium sulfate. The solvent was distilled out at 35-40° C. under reduced pressure to obtain the title compound.
Yield: 2 g
$^1$H NMR: 1.27 (d, 6H), 1.47 (s, 9H), 1.50-1.58 (m, 1H), 2.38 (d, 2H), 3.37 (septet, 1H), 3.51 (d, 3H), 3.57 (s, 3H), 3.63 (bs, 1H), 3.80 (bs, 1H), 4.15-4.18 (m, 1H), 4.44-4.48 (m, 1H), 5.46 (dd, 1H), 6.64 (d, 1H), 7.09 (t, 2H), 7.65 (dd, 2H).

Example 7

PREPARATION OF ETHYL-6-(E)-7-[4-(4-FLUOROPHENYL)-6-ISOPROPYL-2-[N-METHYL-N-METHYLSULFONYLAMINO]PYRIMIDIN-5-YL]-(5S)-HYDROXY-3-OXO HEPTENOATE

Ethyl 6-(E)-7-[4-(4-fluorophenyl)-6-isopropyl-2-[N-methyl-N-methylsulfonylamino]-pyrimidin-5-yl]-(5S)-5-(t-butyldimethylsilyloxy)-3-oxo heptenoate (5 g) in acetonitrile (3 ml) was added to aqueous hydrofluoric acid (6.2 ml, 48% w/w) at 0-5° C. in 15 min. The temperature of the reaction mass was raised to 25-30° C. and stirred for 2 h for completion of silyl cleavage. The reaction mixture was basified with aqueous sodium bicarbonate solution and the product was extracted with ethyl acetate (50 ml). The ethyl acetate layer was washed with water, dried over sodium sulphate and concentrated to give crude product (3 g). The crude product obtained was purified using column chromatography with ethyl acetate/hexane as eluant to yield pure title compound as an oil.
$^1$HNMR (CDCl$_3$, 300 MHz): 1.25 (d, 6H), 1.27-1.29 (t, 3H), 2.65 (d, 2H), 3.34 (septet, 1H), 3.44 (s, 2H), 3.52 (s, 3H), 3.57 (s, 3H), 4.22 (t, 2H), 4.51-4.55 (m, 1H), 5.4 (dd, 1H), 6.64 (d, 1H), 7.08 (m, 2H), 7.63 (dd, 2H).

Example 8

PREPARATION OF (4E)-5-{4-(4-FLUOROPHE-NYL)-6-ISOPROPYL-2-[METHYL-(METHYL-SULFONYL)AMINO]PYRIMIDIN-5-YL}-(3S)-3-(O-TERT-BUTYLDIMETHYLSILYL)-4-PENTENOIC ACID tert-Butyldimethylsilyl chloride (7.6 g, 0.05 mol) was dissolved in N,N-dimethylformamide (25 ml) and anhydrous potassium iodide (8.4 g, 0.05 ml) was added to it at 25° C. The mixture was heated to 60° C. and stirred for 30 min. Triethylamine (7 g, 0.06 mol) was added to the above hot reaction mixture and stirred for 10 min at 60° C. Subsequently (4E)-5-{4-(4-fluorophenyl)-6-isopropyl-2-[methyl(methylsulfonyl)amino]pyridin-5-yl-(3S)-3-hydroxy-4-pentenoic acid (10 g, 0.02 mol) was dissolved in N,N-dimethylformamide (25 ml) and added to the above reaction mixture drop wise over a period of 30 min at 60° C. The reaction mass was further stirred at 60° C. for 2 h and cooled to room temperature. The reaction mass was quenched by adding DM water (50 ml) and product was extracted in toluene (2×50 ml). The toluene layer was washed with aqueous sodium bicarbonate (50 ml) followed by aqueous saturated sodium chloride (50 ml). The solvent was removed under reduced pressure to yield title compound as an oily mass, which was pure enough for the subsequent reaction.

Yield: 12 g (95%)

$^1$HNMR (CDCl$_3$, 300 MHz): 0.05 (s, 6H), 0.89 (s, 9H), 1.27-1.30 (m, 6H), 2.38-2.50 (m, 2H), 3.40 (m, 1H), 3.54 (s, 3H), 3.59 (s, 3H) 4.52 (brs, 1H), 5.50-5.61 (m, 1H), 6.58 (d, 1H), J=15 Hz), 7.0-7.18 (m, 2H), 7.60-7.66 (m, 2H).

Example 9

PREPARATION OF ETHYL (6E)-7-{4-(4-FLUO-ROPHENYL)-6-ISOPROPYL-2-[METHYL-(ME-THYLSULFONYL)AMINO]PYRIMIDIN-5-YL}-(5S)-5-(O-TERTBUTYLDIMETHYLSILYL)-3-OXO-HEPT-6-ENOATE (4E)-5-{4-(4-Fluorophenyl)-6-isopropyl-2-[methyl(methylsulfonyl)amino]pyrimidin-5-yl}-(3S)-3-(O-tert-butyldimethylsilyl)-4-pentenoic acid (10 g, 0.018 mol) was dissolved in tetrahydrofuran (180 ml) and a solution of 1,1-carbonyldiimidazole (5.3 g, 0.03 mol) in tetrahydrofuran (30 ml) was added to the above reaction mass drop wise over a period of 30 min. The reaction mass was stirred overnight and magnesium salt of ethyl malonate (prepared in situ by stirring magnesium alkoxide (2.27 g) and monomethyl malonate (5.0 g) in tetrahydrofuran 30 ml at 25° C.) was added drop wise into the reaction mass. The reaction mass was stirred for additional 20 h. After completion of the reaction, tetrahydrofuran was distilled out and redissolved the mass in a mixture of toluene (500 ml) and ethyl acetate (100 ml). The resulting organic layer was washed with aqueous sodium carbonate (500 ml) followed by DM water (2×500 ml). Thereafter, the organic layer was concentrated completely at 45-50° C. under reduced pressure to obtain the crude title compound. The crude compound obtained was used for the subsequent reaction without further purification.

Yield: 8.75 g

Example 10

PREPARATION OF ETHYL (6E)-7-{4-(4-FLUO-ROPHENYL)-6-ISOPROPYL-2-[METHYL(ME-THYLSULFONYL)AMINO]PYRIMIDIN-5-YL}-(5S)-5-HYDROXY-3-OXO HEPT-6-ENOATE

Ethyl (6E)-{4-(4-fluorophenyl)-6-isopropyl-2-[methyl(methylsulfonyl)amino]pyrimidin-5-yl}-(5S)-5-(O-tertbutyldimethylsilyl)-3-oxo-hept-6-enoate (10 g, 0.016 mol) was dissolved in acetonitrile (250 ml) at 25° C. and the reaction mixture was cooled to 0° C. Hydrofluoric acid (48%, 15 ml) was diluted in acetonitrile (250 ml) and added slowly to the above reaction mass over a period of 20 min at 0-5° C. After addition, the reaction mass was quenched by addition of 10% aqueous sodium bicarbonate solution (50 ml). The organic layer was separated and the aqueous layer was extracted with ethyl acetate (50 ml). The combined organic layer was washed with DM water (50 ml) and solvent distilled out under vacuum at 40-45° C. to obtain the product as an oily mass.

Yield: 8.25 g (66%)

$^1$HNMR (CDCl$_3$, 300 MHz): 1.25-1.32 (m, 9H), 2.67 (d, 2H, J=6 Hz), 3.30-3.39 (m, 1H), 3.46 (s, 2H), 3.53 (s, 3H), 3.59 (s, 3H), 4.12-4.20 (m, 2H), 4.56 (brs, 1H), 5.40 (dd, J=15 Hz, 6 Hz), 6.68 (d, J=15 Hz, 1H), 7.09-7.28 (m, 2H), 7.62-7.67 (m, 2H).

Example 11

PREPARATION OF ETHYL (6E)-7-{4-(4-FLUO-ROPHENYL)-6-ISOPROPYL-2-[METHYL-(ME-THYLSULFONYL)AMINO]PYRIMIDIN-5-YL} (3R,5S)-3,5-DIHYDROXY-HEPT-6-ENOATE

Ethyl (6E)-7-{4-(4-fluorophenyl)-6-isopropyl-2-[methyl-(methylsulfonyl)amino]pyrimidin-5-yl}(5S)-3-oxo-hept-6-enoate (10 g, 0.02 mol) was dissolved in a mixture of tetrahydrofuran (500 ml) and methanol (70 ml) at 25° C. The mixture was cooled to −78° C. and diethylmethoxyborane (48% in tetrahydrofuran, 5 ml, 0.02 mol) was added to the above cooled reaction mass at −75° C. to −78° C. over a period of 20 min. The reaction mass was stirred at −75° C. to −78° C. for 30 min before adding sodium borohydride (1 g, 0.02 m). The mixture was stirred for another 2 h at −78° C. and quenched by adding acetic acid (13 g). Thereafter, saturated sodium bicarbonate solution (500 ml) was added to it and the organic layer was separated from the aqueous layer. The aqueous layer was extracted with ethyl acetate (250 ml) and the combined organic layer was washed with DM water (250 ml). The organic layer obtained during the above process was concentrated at 40-45° C. under vacuum to get the crude product, which was used for hydrolysis as such without further purification.

Yield: 10 g (99%)

$^1$HNMR (CDCl$_3$, 300 MHz): 1.22-1.30 (m, 9H), 1.46-1.53 (m, 2H), 2.46 (d, J=6 Hz, 2H), 3.34-3.38 (m, 1H), 3.52 (s, 3H), 3.58 (s, 3H), 4.15-4.28 (m, 2H), 4.95 (brs, 1H), 5.45 (dd, J=15 Hz, 6 Hz).

Example 12

PREPARATION OF ETHYL (6E)-7-(4-(4-FLUO-ROPHENYL)-6-ISOPROPYL-2-[METHYL(ME-THYLSULFONYL)AMINOPYRIMIDIN-5-YL] (3R,5S)-3,5-DIHYDROXYHEPT-6-ENOATE BENZATHINE SALT

Ethyl (6E)-7-(4-(4-fluorophenyl)-6-isopropyl-2-[methyl (methylsulfonyl)aminopyrimidin-5-yl]-(3R,5S)-3,5-dihydroxyhept-6-enoate (1 g) was dissolved in ethanol (12 ml) at 25-30° C. and added 0.1N NaOH (16 ml) in 15 min at 25-30° C. under reduced pressure. The reaction mixture was stirred for 2½ h at 25-30° C. and ethanol was removed completely. Under reduce pressure DM water (25 ml) was added to the concentrated mass and washed with toluene (2×50 ml). Finally the aqueous layer was washed with 30% ethyl acetate and toluene mixture (2×50 ml). To the aqueous layer added a solution of benzathine diacetate (1 g) dissolved in DM water (10 ml) at 25-30° C. and stirred for 3 hrs at 25-30° C. The resulting product was filtered, washed with DM water (5 ml) and dried to constant weight to yield the title compound.

Yield: 10.6 g.

Example 13

PREPARATION OF ROSUVASTATIN CALCIUM

N,N-Dibenzylethylenediamine rosuvastatin salt (2 g) was dissolved in a mixture of ethyl acetate (30 ml) and DM water (30 ml) and cooled to 0-5° C. The above cold mixture was treated with aqueous hydrochloric acid (3 ml) at 0-5° C. The resulting clear solution was stirred for 10 min. The organic layer was separated, washed with water and cooled to 0-5° C. Aqueous sodium hydroxide (1 N, 30 ml) was added to the above organic layer and stirred at room temperature for 30 min for conversion of rosuvastatin acid to it sodium salt. Toluene (70 ml) was added to the above mixture and stirred for 10 min. The aqueous layer was separated and traces of solvent were removed at 40-45° C. under vacuum. The resulting clear aqueous layer was treated with an aqueous solution of calcium chloride (1N, 3 ml) and resulting rosuvastatin calcium was filtered and dried.

Yield: 0.6 g

Chromatographic purity: 99.3%.

Example 14

PREPARATION OF ROSUVASTATIN CALCIUM (3R,5S)-7-[4-(4-fluorophenyl)-6-isopropyl-2-[N-methyl-N-methylsulfonylamino]pyrimidin-5-yl]-3,5-dihydroxy-(6E)-heptenoic acid ethyl ester (5 g) was dissolved in a mixture of ethanol (25 ml) and tetrahydrofuran (2.5 ml) at 20-25° C. under stirring. The reaction mass was cooled to 10-15° C. and 1 N aqueous sodium hydroxide solution (9.82 ml) was added slowly at 10-15° C. over a period of 20-25 min. Thereafter, the reaction mass was stirred for 2-3 h at 20-25° C. and then concentrated under reduced pressure. A mixture of water (48 ml), ethanol (1.5 ml) and tetrahydrofuran (1 ml) was added to the above reaction mass. The reaction mass was washed with a mixture of toluene (30 ml) and ethylacetate (20 ml). After washing, the aqueous layer was concentrated to a volume of approximately 35 ml at 35-40° C. and cooled to 25-30° C. Aqueous calcium chloride (25 ml) (1.44 g of calcium chloride dihydrate was dissolved in 14 ml of water and the volume was make up to 25 ml) was added to the above aqueous layer at 25-30° C. over a period of ½ hr and stirred the suspension for 3 h. The product obtained was filtered and dried under reduced pressure at 35-40° C. till the moisture content is approximately 1.8 to 2%

Yield: 3.5 g .

Example 15

PREPARATION OF (3S)-5-[4-(4-FLUOROPHE-NYL)-6-ISOPROPYL-2-(N-METHYL-N-METH-YLSULFONYLAMINO)PYRIMIDIN-5-YL]-3-HYDROXY-4-PENTENOIC ACID (1S)-2-HYDROXY-1,2,2-TRIPHENYLETHYL ESTER

A mixture of hexamethyldisilazane (33.5 ml, 0.15 mol) and tetrahydrofuran (50 ml) was cooled to −10° C. under nitrogen atmosphere. n-Butyllithium (3.92 ml, 14% in Hexanes) was added over a period of 20 min (Exothermic), keeping the temperature below 0° C. The reaction mixture was stirred at 0 to −5° C. for 15 min and then cooled to −35° C. before adding 2-(S)-acetoxy-1,1,2-triphenylethanol (4.84 g, 0.014 mol) over a period of 5 min. The temperature of the reaction mixture was allowed to go up to −15° C. and stirred for 45 min. The resulting homogeneous yellow solution was cooled to −78° C. and a solution of (2E)-3-[4-(4-fluorophenyl-6-isopropyl-2-(N-methyl-N-methylsulfonylamino)pyrimidin-5-yl]-propenal (5 g, 0.013 mol) in tetrahydrofuran (20 ml) was added over a period of 30 min maintaining the temperature at −75 to −78° C. The reaction mixture was stirred for 40 min at −78° C. and then slowly raised the temperature to 0° C. over a period of 20 min. The reaction mass was quenched by adding aqueous hydrochloric acid (5N, 30 ml). The organic layer was separated and the aqueous layer was extracted with ethyl acetate (50 ml). The combined organic extracts were washed with saturated sodium chloride solution (50 ml) and evaporated to get a solid mass. The product obtained from the above process was crystallized from hexane:ethyl acetate (9:1 v/v, 50 ml).

Yield: 9.0 g $^1$H NMR (300 MHz, CDCl$_3$): 1.26 (d, J=6 Hz, 6H), 2.37 (d, J=6 Hz, 2H), 2.70 (brs, 1H), 2.84 (s, 1H), 3.30-3.35 (m, 1H), 3.53 (s, 3H), 3.59 (s, 3H), 4.44 (brs, 1H), 5.37 (dd, J=16, 5 Hz, 1H), 6.6 (d, J=16 Hz, 1H), 6.7 (s, 1H), 7.05-7.19 (m, 15H), 7.28-7.38 (m, 2H), 7.58-7.59 (m, 2H).

Example 16

PREPARATION OF (4E)-5-{4-(4-FLUOROPHE-NYL)-6-ISOPROPYL-2-(N-METHYL-N-METH-YLSULFONYLAMINO)-PYRIMIDIN-5-YL}-3-HYDROXY-4-PENTENOIC ACID (3S)-5-[4-(4-fluorophenyl)-6-isopropyl-2-(N-methyl-N-methylsulfonylamino)pyrimidin-5-yl]-3-hydroxy-4-pentenoic acid (1S)-2-hydroxy-1,2,2-triphenylethyl ester (25 g) was dissolved in a mixture of tetrahydrofuran (75 ml) and methanol (50 ml) at 25-30° C. 1N aqueous sodium hydroxide solution (37 ml) was added dropwise to the above reaction mass over a period of 30 min at 25-30° C. It was stirred at 25-30° C. and monitored the progress of the reaction by TLC (n-Hexane-Ethyl acetate: 7:3 v/v). After completion, the solvent was removed at 45-50° C. under reduced pressure to obtain a residue, which was suspended in water (125 ml). It was subsequently estracted with methylene chloride (2×25 ml) at 25-30° C. Thereafter the resulting aqueous layer was acidified with 1 N aqueous hydrochloric acid (~18 ml) to pH 3-4 at 25-30° C. The above aqueous layer was extracted with methylene chloride (2×50 ml) at 25-30° C. and the combined methylene chloride layer was washed with aqueous sodium chloride (25% w/v, 60 ml). The crude product was isolated by distilling methylene chloride at 35-40° C. as viscous oil, which was subsequently recrystallised from hexanes to yield the title compound. This compound was used as such for further purification to get better chiral purity.

Yield: 17 gm

Example 17

PREPARATION OF (4E)-5-{4-(4-FLUOROPHENYL)-6-ISOPROPYL-2-(N-METHYL-N-METHYLSULFONYLAMINO)PYRIMIDIN-5-YL}-(3S)-3-HYDROXY-4-PENTENOIC ACID, (α)-METHYLBENZYLAMINE SALT (4E)-5-{4-(4-Fluorophenyl)-6-isopropyl-2-(N-methyl-N-methylsulfonylamino)-pyrimidin-5-yl}-3-hydroxy-4-pentenoic acid (100 gm, 0.228 ml) which contains predominantly S-isomer was dissolved in acetonitrile (1 litre) and R-(+)-α-methylbenzylamine (27.7 gm, 0.228 ml) was added to it dropwise over a period of 30 min during which salt precipitated out. The above suspension was heated to 70-75° C. and water (75 ml) was added to it to get a clear solution, which was subsequently cooled to 25° C. to reprecipitate the product. It was further cooled to 5-10° C., filtered and washed with chilled acetonitrile (150 ml, 5-10° C.). The product obtained was dried at 40-45° C. under vacuum to constant weight.

Yield: 95 gm, (74%)

Purity: >99.5%

Chiral Purity: >99.5% ee

SOR: $[\alpha]^{20}$, +5.24 (c=1% in methanol)

$^1$HNMR (CDCl$_3$, 300 MHz): 1.20 (d, J=7 Hz, 6H, (CH$_3$)$_2$), 1.36 (d, J=7 Hz, 3H, CH$_3$), 2.0-2.12 (m, 2H, CH$_2$), 3.38-3.42 (m, 1H, —CH), 3.45 (s, 3H, CH$_3$), 3.55 (s, 3H, CH$_3$), 4.1-4.2 (m, 1H), CH), 4.29-4.45 (m, 1H, CH), 5.52 (dd, J=16; 6 Hz, 1H, CH), 6.54 (d, J=16 Hz, 1H, CH), 7.25-7.69 (m, 7H, ArH), 7.71-7.74 (m, 1H, ArH).

Example 18

PREPARATION OF (4E)-5-{4-(4-FLUOROPHENYL)-6-ISOPROPYL-2-(N-METHYL-N-METHYLSULFONYLAMINO]PYRIMIDIN-5-YL}-(3S)-3-HYDROXY-4-PENTENOIC ACID (4E)-5-{4-(4-Fluorophenyl)-6-isopropyl-2-[methyl(methylsulfonyl)amino]pyrimidin-5-yl}-(3S)-3-hydroxy-4-pentenoic acid, α-methylbenzylamine salt (75 gm, 0.134 mol) was suspended in a mixture of methylene chloride (125 ml) and water (125 ml) at 25° C. The above suspension was cooled to 2-5° C. and pH was adjusted to 3-3.5 by slow addition of 1N aqueous Hydrochloric acid. Thereafter the organic layer was separated, washed with water (125 ml) and evaporated to dryness to get the pure product.

Yield: 57 gm (97%).

We claim:

1. A process for preparing (E)-7-[4-(4-fluorophenyl)-6-isopropyl-2-[methyl(methylsulfonyl)amino]pyrimidin-5-yl] (3R,5S)-3,5-dihydroxyhept-6-enoic acid calcium of Formula I,

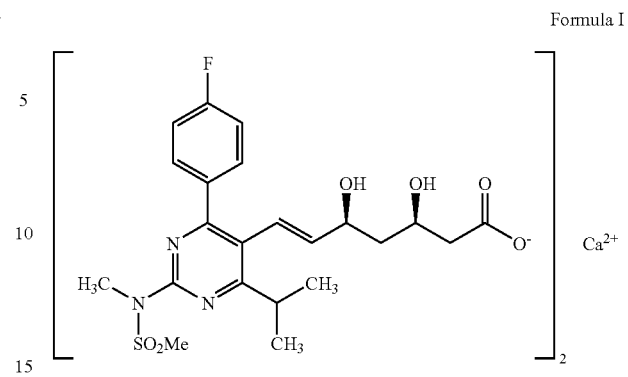

Formula I which comprises, a) protecting the compound of Formula III with a suitable hydroxy protecting group

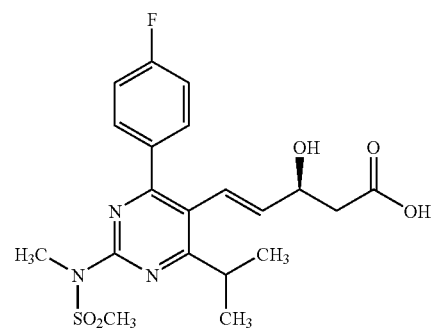

Formula III in an organic solvent to obtain a compound of Formula IV,

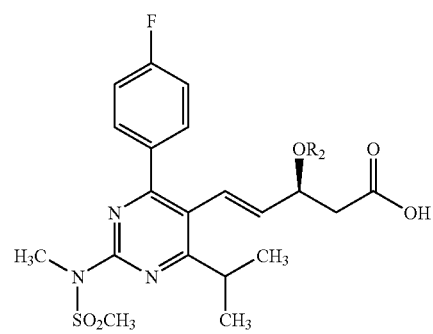

Formula IV wherein R$_2$ represents a hydroxy protecting group;

b) activating the acid group of the compound of Formula IV with acid activator, followed by treating the resulting intermediate with a metal complex of Formula V,

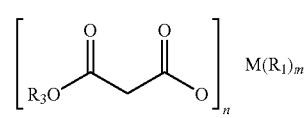

Formula V wherein R$_3$ represents C$_1$-C$_4$ straight chain or branched chain alkyl, aryl, substituted aryl, aralkyl; M represents Mg, Zn, Ca, Cu; n represents an integer selected from 1-2; $R_1$ represents alkyl or alkoxy; m represents an integer selected from 0 or 1; in an organic solvent to obtain a compound of Formula VI, Formula VI

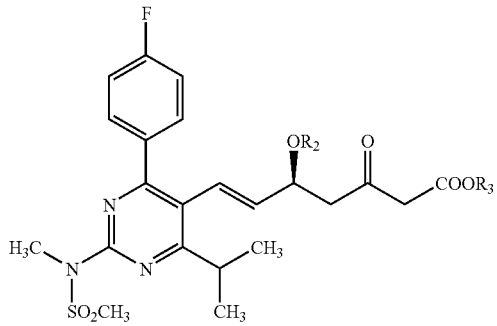

wherein $R_2$ and $R_3$ are as defined above;

c) deprotecting the compound of Formula VI with a suitable reagent in an organic solvent, water or mixtures thereof to obtain compound of Formula VII, Formula VII

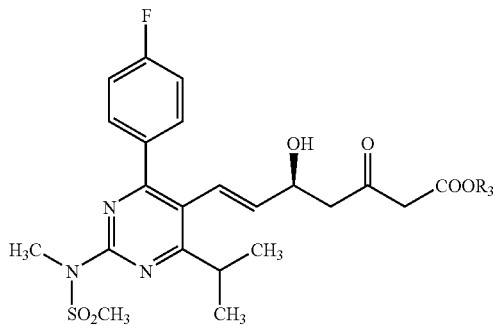

wherein $R_3$ is as defined above;

d) reducing the compound of Formula VII to obtain a compound of Formula VIII,

Formula VIII

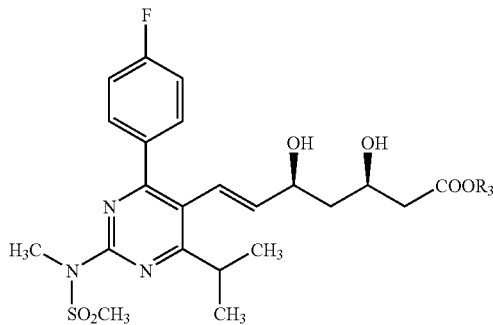

wherein $R_3$ as defined above;

e) hydrolyzing the compound of Formula VIII and then treating with a source of calcium ions to obtain a compound of Formula I.

2. The process according to claim 1, wherein protecting group employed is selected from tert-butyldimethylsilyl chloride, dihydropyran, trimethylsilyl chloride, and methoxy methyl chloride.

3. The process according to claim 1, wherein the solvent employed in step (a) is selected from tetrahydrofuran, dioxane, dimethoxy ethane, dichloromethane, ethylene dichloride, dimethyl formamide, dimethylsulfoxide, N-methyl pyrrolidinone, sulfolane and mixtures thereof.

4. The process according to claim 1, wherein the activating group employed in step (b) is 1,1-carbonyldiimidazole, methyl chloroformate, ethyl chloroformate, phenyl chloroformate, 4-methoxyphenylchloroformate, 4-chlorophenylchloroformate, 2,4-dinitrophenylchloroformate, 4-trifluoromethylphenylchloroformate, 4-nitrophenylchloroformate or 2-nitrophenylchloroformate.

5. The process according to claim 1, wherein the solvent employed in step (b) is selected from tetrahydrofuran, methyl tert.butylether, isopropyl ether, diisopropyl ether, N,N-dimethylformamide, methylene dichloride, acetonitrile, toluene, xylene, hexane and mixtures thereof.

6. The process according to claim 1, wherein the deprotection reaction is carried out using hydrofluoric acid, lithium fluoride, potassium fluoride, sodium fluoride, sulfonic acids such as para toluene sulfonic acids, methanesulfonic acids, trifluormethane sulfonic acid, organic acids such as formic acid, trifluoro acetic acid, acetic acid or tetrabutyl ammonium fluoride.

7. The process according to claim 1, wherein the organic solvent used in step (c) is selected from tetrahydrofuran, acetonitrile, methanol, ethanol, methylene chloride, ethylene dichloride, toluene, xylene, and mixtures thereof.

8. The process according to claim 1, wherein the reduction in step (d) is carried out using metal borohydrides selected from sodium borohydride, potassium borohydride and calcium borohydrate.

9. The process according to claim 1, wherein the chelating agent used in step (d) is selected from trialkylborane or boronates selected from diethyl methoxy borane, dimethyl methoxy borane, diethyl ethoxy borane and dimethyl ethoxy borane.

10. The process according to claim 1, wherein the reduction in step (d) is carried out in an inert solvent selected from tetrahydrofuran, lower alkanol and mixtures thereof.

11. The process according to claim 1, wherein the hydrolysis of step (e) is carried out using alkali metal hydroxides selected from sodium hydroxide, potassium hydroxide or calcium hydroxide.

12. A process for preparing (E)-7-[4-(4-fluorophenyl)-6-isopropyl-2-[methyl(methylsulfonyl)amino]pyrimidin-5-yl] (3R,5S)-3,5-dihydroxyhept-6-enoic acid calcium of Formula I,

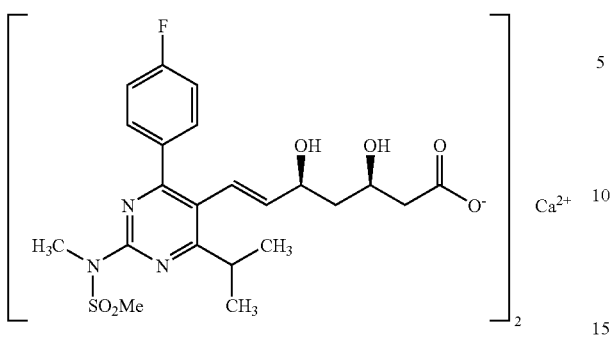

Formula I which comprises,
 a) protecting the compound of Formula III with a suitable hydroxy protecting group

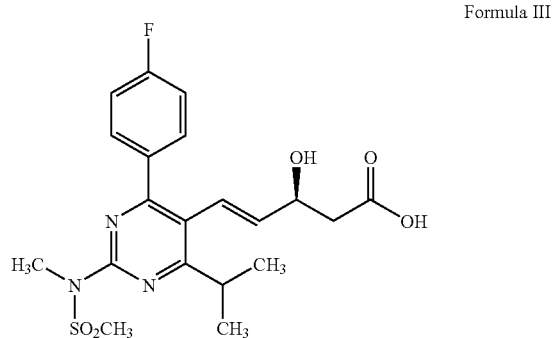

Formula III in an organic solvent to obtain a compound of Formula IV,

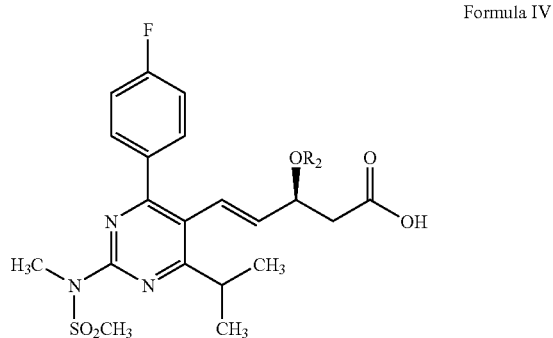

Formula IV wherein $R_2$ represents a hydroxy protecting group;
 b) activating the acid group of the compound of Formula IV with acid activator, followed by treating the resulting intermediate with a metal complex of Formula Va,

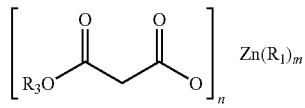

Formula Va wherein $R_3$ represents $C_1$-$C_4$ straight chain or branched chain alkyl, aryl, substituted aryl, aralkyl; n represents an integer selected from 1-3; $R_1$ represents alkyl or alkoxy; m represents an integer selected from 0 or 1; in an organic solvent to obtain a compound of Formula VI,

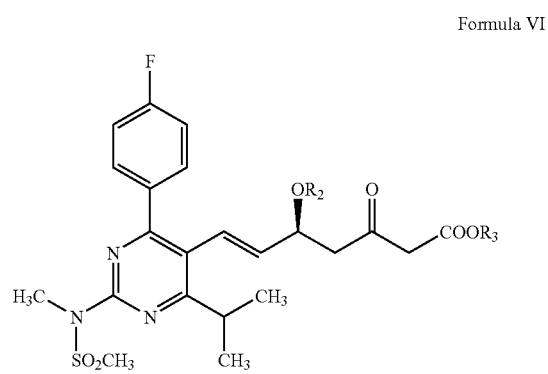

Formula VI wherein $R_2$ and $R_3$ are as defined above;
 c) deprotecting the compound of Formula VI with a suitable reagent in an organic solvent, water or mixtures thereof to obtain compound of Formula VII,

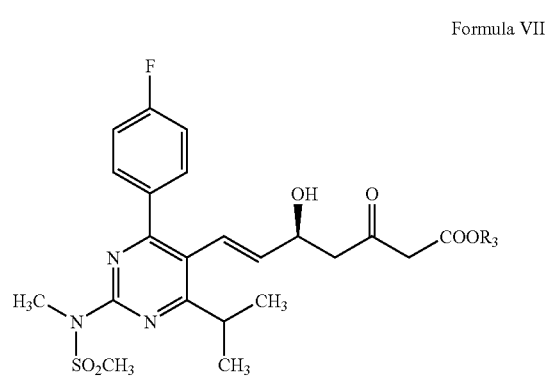

Formula VII wherein $R_3$ is as defined above;
 d) reducing the compound of Formula VII to obtain a compound of Formula VIII,

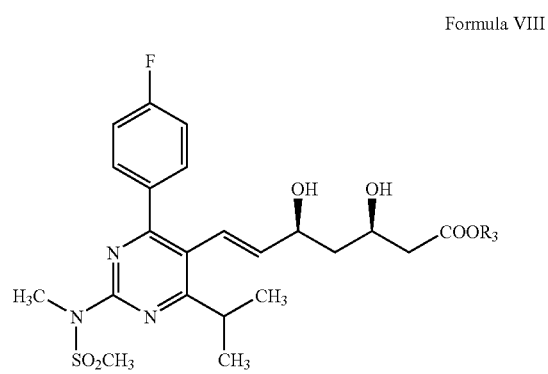

Formula VIII wherein $R_3$ as defined above;
 e) hydrolyzing the compound of Formula VIII and then treating with a source of calcium ions to obtain a compound of Formula I.

13. The process according to claim 12, wherein protecting group employed is selected from tert-butyldimethylsilyl chloride, dihydropyran, trimethylsilyl chloride and methoxy methyl chloride.

14. The process according to claim 12, wherein the solvent employed in step (a) is selected from tetrahydrofuran, dioxane, dimethoxy ethane, dichloromethane, ethylene dichloride, dimethyl formamide, dimethylsulfoxide, N-methylpyrrolidinone, sulfolane and mixtures thereof.

15. The process according to claim 12, wherein the activating group employed in step (b) is 1,1-carbonyldiimidazole, methyl chloroformate, ethyl chloroformate, phenyl chloroformate, 4-methoxyphenylchloroformate, 4-chlorophenylchloroformate, 2,4-dinitrophenylchloroformate, 4-trifluoromethylphenylchloroformate, 4-nitrophenylchloroformate or 2-nitrophenylchloroformate.

16. The process according to claim 12, wherein the solvent employed in step (b) is selected from tetrahydrofuran, methyl tert.butylether, isopropyl ether, diisopropyl ether, N,N-dimethylformamide, methylene dichloride, acetonitrile, toluene, xylene, hexane and mixtures thereof.

17. The process according to claim 12, wherein the deprotection reaction is carried out using hydrofluoric acid, lithium fluoride, potassium fluoride, sodium fluoride, sulfonic acids such as para toluene sulfonic acids, methanesulfonic acids, trifluormethane sulfonic acid, organic acids such as formic acid, trifluoro acetic acid, acetic acid; or tetrabutyl ammonium fluoride.

18. The process according to claim 12, wherein the organic solvent used in step (c) is selected from tetrahydrofuran, acetonitrile, methanol, ethanol, methylene chloride, ethylene dichloride, toluene, xylene, and mixtures thereof.

19. The process according to claim 12, wherein the reduction in step (d) is carried out using metal borohydrides selected from sodium borohydride, potassium borohydride and calcium borohydrate.

20. The process according to claim 12, wherein the chelating agent used in step (d) is selected from trialkylborane and dialkyl alkoxy boranes selected from diethyl methoxy borane, dimethyl methoxy borane, diethyl ethoxy borane and dimethyl ethoxy borane.

21. The process according to claim 12, wherein the reduction in step (d) is carried out in an inert solvent selected from tetrahydrofuran, lower alkanol and mixtures thereof.

22. The process according to claim 12, wherein the hydrolysis of step (e) is carried out using alkali metal hydroxides selected from sodium hydroxide, potassium hydroxide or calcium hydroxide.

23. A process for preparing (E)-7-[4-(4-fluorophenyl)-6-isopropyl-2-[methyl(methylsulfonyl)amino]pyrimidin-5-yl] (3R,5S)-3,5-dihydroxyhept-6-enoic acid calcium of Formula I,

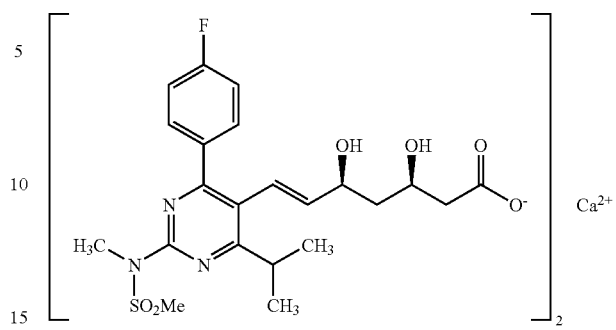

Formula I which comprises, a) protecting the compound of Formula III

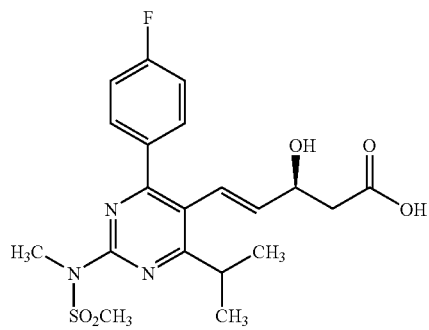

Formula III with tert-butyldimethylsilyl chloride in the presence of N,N-dimethylformamide, potassium iodide and triethylamine to obtain a compound of Formula XII,

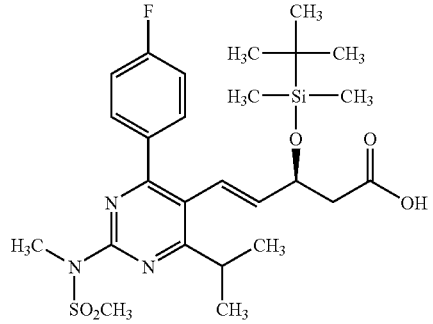

Formula XII b) activating the acid group of the compound of Formula XII with 1,1-carbonyldiimidazole in tetrahydrofuran, followed by treating the resulting intermediate with a Zinc salt of ethyl malonate to obtain a compound of Formula XIII, Formula XIII

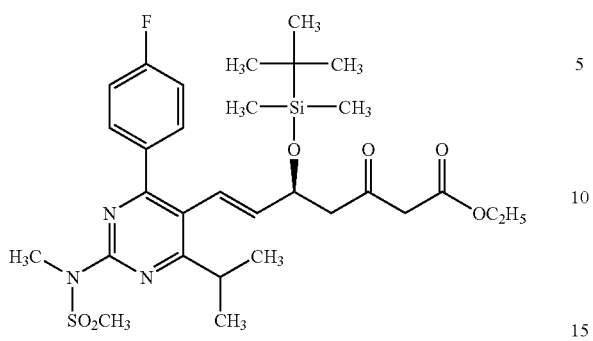

c) deprotecting the compound of Formula XIII with hydrofluoric acid in acetonitrile to obtain compound of Formula XIV, Formula XIV

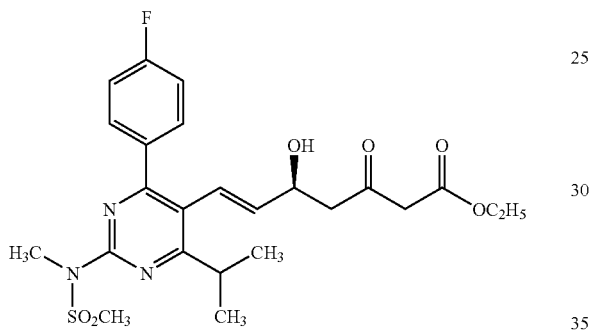

d) reducing the compound of Formula XIV using sodium borohydride, diethylmethoxyborane in tetrahydrofuran to obtain a compound of Formula XV, Formula XV

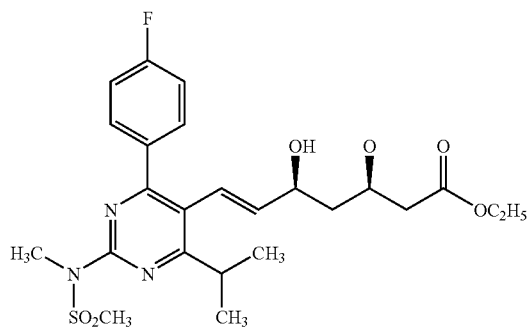

e) hydrolyzing the compound of Formula XV using sodium hydroxide in a mixture of ethanol and tetrahydrofuran and then treating with aqueous calcium chloride to obtain a compound of Formula I.

\* \* \* \* \*